United States Patent [19]

Sien et al.

[11] 4,388,408
[45] Jun. 14, 1983

[54] COKER FEEDSTOCK ANALYSIS METHOD

[75] Inventors: Herbert P. Sien, Philadelphia, Pa.; Thomas J. McGinley, Wilmington, Del.

[73] Assignee: Suntech, Inc., Philadelphia, Pa.

[21] Appl. No.: 219,406

[22] Filed: Dec. 22, 1980

[51] Int. Cl.³ ............................................. G01N 33/26
[52] U.S. Cl. ................................. 436/60; 73/61.1 R; 208/50; 250/373; 436/161
[58] Field of Search ................... 23/230 HC, 230 M; 208/50; 73/61.1 R; 250/301, 373; 436/60, 2, 161

[56] References Cited

U.S. PATENT DOCUMENTS 3,205,353 9/1965 Bray ................................ 250/301 X
3,326,796 6/1967 Muller ................................ 208/50
4,043,098 8/1977 Kegler ................................ 208/50
4,238,451 12/1980 Ciais et al. ................. 23/230 HC X

FOREIGN PATENT DOCUMENTS 938312 10/1963 United Kingdom .

OTHER PUBLICATIONS

Skoog, et al., "Analytical Chemistry-An Introduction," Holt, Rinehart and Winston, New York, 1965, pp. 473-475.
Zimmerman, Analytical Chemistry, vol. 34, No. 6, May 1962, pp. 710-711.
ASTM Designation: D 2007-64, 1964, "Characteristic Groups in Rubber Extender and Processing Oils By The Clay-Gel Adsorption Chromatographic Method".
ASTM Designation: D 2008-64T, 1964, "Ultraviolet Absorbance Absorptivity Of Petroleum Products."

Primary Examiner—Arnold Turk
Attorney, Agent, or Firm—J. Edward Hess; Donald R. Johnson; Paul Lipsitz

[57] ABSTRACT

A clarified slurry oil coker feedstock is subjected to absorption chromatography and ultraviolet light absorptivity and the results are correlated to determine the suitability of the feedstock for electrode grade coke.

3 Claims, No Drawings

COKER FEEDSTOCK ANALYSIS METHOD

Graphite electrodes are required to have low coefficients of thermal expansion (CTE) to withstand the increasingly severe conditions of thermal shock and stress encountered in the operation of electric steel furnaces. The performance of these electrodes depends to a large degree on the characteristics of the filler coke (needle coke), which is conventionally produced by the delayed coking of selected heavy refinery feedstocks, in particular, clarified slurry oil (i.e., decant oil) from fluidized bed catalytic cracking operations. A coke suitable for use in graphite electrode manufacture must be low in sulfur, low in metals, highly crystalline, and as dense as possible. To meet the coke properties requirements, coker feedstocks must be carefully selected. However, the determination of whether or not a feedstock will make a low CTE electrode is very difficult.

In order to produce premium needle coke for graphite electrode manufacture, the coker feedstock should be highly aromatic and have a low content of insoluble components. To date no simple laboratory or small scale test exists which could be used to predict or relate, with any degree of certainty, the suitability of a feedstock for needle coke manufacture. The only technique which has been found of value in evaluating feedstocks for electrode grade coke manufacture, and which is used extensively by all needle coke customers, is the manufacture of the coke, the fabrication of test graphite electrodes, therefrom, and the actual subjection of the electrodes to suitable tests such as CTE and electric resistivity. This method, however, because of its complexity, is far from simple to perform for either the needle coke user or supplier.

In British Pat. No. 938,312 a method is disclosed for preparing a feedstock for use in the production of electrode grade coke by blending at least two hydrocarbon fractions having different quality indexes in relative proportions to provide a feedstock having a "Quality Index" of at least 0.080. We have found that that method, when applied to a number of decant oils, cannot differentiate the low CTE precursors from the high CTE precursors.

U.S. Pat. No. 3,326,796 (N. William Muller; issued June 20, 1967; Class 208-50) discloses a coker feedstock characterized by the parameters of benzene solubles, pentane solubles, sulfur, Conradson carbon, specific gravity and softening point.

U.S. Pat. No. 4,043,898 (William H. Kegler, issued Aug. 23, 1977; Class 208-50) discloses a characterization of a coker feedstock for suitability prior to coking based on volumetric average boiling point and API gravity.

The present invention provides a simple method to determine with good accuracy the suitability of a clarified slurry oil feedstock for making electrode grade coke and further provides means for controlling and producing more needle coke of constant and improved quality.

In accord with the invention a hydrocarbon coker feedstock is classified by asphaltene content and ultraviolet (U.V.) absorptivity to select suitable feedstocks. The hydrocarbon feedstock which is subjected for testing in accord with the invention will be a clarified slurry oil from fluidized bed catalytic cracking operations which is used as a fresh feed to the coker unit. Suitable coker feedstocks are those which when subjected to asphaltene and ultraviolet absorption analyses show no more than 12 weight percent of asphaltenes and minimum absorptivity in a 1 cm. cell of 40, 19 and 15 liters per gm-cm. at wave lengths of 292, 324 and 340 nm., respectively.

Asphaltenes are determined by pentane solubility or by absorption chromatography in a clay/silica gel column to separate the asphaltenes in the clarified slurry oil in accord with the standard ASTM D2007 test method.

Ultraviolet absorption analyses is made by the standard ASTM D2008 test method at specified wavelengths in the ultraviolet spectrum to characterize the absorptivity of the petroleum products. Most polynuclear aromatics have their principal wavelengths between 280 and 400 millimicrons.

Using the above analytical methods on a clarified slurry oil used for coking, data was obtained on suitable and unsuitable coker feeds and such data is shown in Table I.

TABLE I

CLARIFIED SLURRY OIL ANALYSES

| SAMPLE No. | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| Asphaltenes (wt. %) | 5.1 | 7.4 | 11.9 | 10.7 | 6.8 | 16.3 | 8.7 | 6.0 | 45.9 | 0.3 | 4.1 | 10.6 | 6.6 | 6.8 | 5.1 |
| UV Absorptivity (L/gm-cm) | | | | | | | | | | | | | | | |
| @ 292 nm | 34.2 | 45.4 | 44.3 | 41.8 | 33.8 | 39.6 | 38.1 | 35.7 | 57.4 | 26.8 | 30.7 | 31.6 | 35.1 | 36.8 | 36.6 |
| @ 324 nm | 15.6 | 19.4 | 20.0 | 19.7 | 15.5 | 18.5 | 17.8 | 16.7 | 27.2 | 9.91 | 13.9 | 14.1 | 16.0 | 16.8 | 16.4 |
| @ 340 nm | 13.0 | 16.8 | 15.7 | 17.5 | 12.8 | 15.1 | 14.1 | 13.9 | 21.7 | 8.99 | 11.1 | 11.7 | 13.9 | 14.7 | 14.5 |
| ELECTRODE QUALITY | Good | Good | Good | Good | Poor | Poor | Poor | Poor | Poor | Poor | Poor | Poor | Poor | Poor | Poor |

It will be noted that Sample No. 1, which gave a good needle coke product, is somewhat inconsistent with the criteria established by the process of this invention in that the U.V. absorptivity is below the required values, but the remaining examples establish that use of the asphaltene content and U.V. absorptivity parameters are useful criteria for determining a suitable feedstock for electrode grade coke.

The invention claimed is:

1. A method for determining the suitability of a clarified slurry oil from a fluidized bed catalytic cracking operation as a feedstock for electrode grade coke which comprises subjecting said feedstock to analysis of asphaltenes and U.V. absorptivity and selecting as suitable for coking those oils which show no more than 12 weight percent of asphaltenes and a minimum absorptivity in a 1 cm. cell of 40, 19 and 15 liters per gm-cm., at wave lengths of 292, 324 and 340 nm., respectively.

2. The method of claim 1 wherein asphaltenes are determined by pentane solubility.

3. The method of claim 1 wherein asphaltenes are determined by absorption chromatography in a clay-silica gel column.

* * * * *